(12) United States Patent
Wasson et al.

(10) Patent No.: US 7,065,939 B2
(45) Date of Patent: Jun. 27, 2006

(54) METHOD OF WRAPPING DIGITAL TAMPONS

(75) Inventors: Matthew Howard Wasson, Cincinnati, OH (US); Holger Wendt, Crailsheim (DE); Francis Michael Nicholas, Addlestone (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/003,590

(22) Filed: Dec. 3, 2004

(65) Prior Publication Data

US 2006/0048484 A1 Mar. 9, 2006

Related U.S. Application Data

(63) Continuation-in-part of application No. 10/934,173, filed on Sep. 3, 2004, now abandoned.

(51) Int. Cl.
*B65B 9/06* (2006.01)

(52) U.S. Cl. .............. 53/450; 53/550; 604/385.02; 604/385.18

(58) Field of Classification Search ............... 53/450, 53/550; 604/385.02, 385.18
See application file for complete search history.

(56) References Cited

U.S. PATENT DOCUMENTS

| | | | |
|---|---|---|---|
| 3,818,912 A | 6/1974 | Etz | |
| 3,863,636 A | 2/1975 | Johnson | |
| 4,370,844 A * | 2/1983 | Degn et al. | 53/550 |
| 4,648,513 A * | 3/1987 | Newman | 604/385.02 |
| 5,471,820 A | 12/1995 | Oppe | |
| 6,170,237 B1 * | 1/2001 | Wipf | 53/550 |
| 6,186,995 B1 * | 2/2001 | Tharpe, Jr. | 604/385.18 |

FOREIGN PATENT DOCUMENTS

| | | | |
|---|---|---|---|
| JP | 01226506 A | * | 9/1989 |
| JP | 05170210 A | * | 7/1993 |
| WO | WO 96/23711 | | 8/1996 |

OTHER PUBLICATIONS

PCT International Search Report, Feb. 16, 2006.

* cited by examiner

*Primary Examiner*—Stephen F. Gerrity
(74) *Attorney, Agent, or Firm*—James E. Oehlenschlager; Michael S. Kolodesh; David M. Weirich

(57) ABSTRACT

A method of individually wrapping digital tampons having a withdrawal string attached thereto is disclosed. The method includes a multiplicity of transporting devices for transporting digital tampons in a machine direction and for holding withdrawal strings attached to the tampons such that the withdrawal strings do not interfere with the subsequent wrapping operations.

6 Claims, 6 Drawing Sheets

METHOD OF WRAPPING DIGITAL TAMPONS

CROSS REFERENCE TO RELATED APPLICATIONS

This application is a continuation-in-part of prior U.S. application Ser. No. 10/934,173 filed on Sep. 3, 2004 (now abandoned).

FIELD OF THE INVENTION

The present invention relates to a method of wrapping digital tampons, including catamenial digital tampons.

BACKGROUND OF THE INVENTION

Digital tampons, including catamenial digital tampons, have been used for inserting into body cavities (such as vagina and the like) by the fingers of the user, and without the aid of an inserting device. After the use, the tampon is withdrawn from the body cavity by pulling a withdrawal string attached to the tampon and extending from the body cavity. Typically, the withdrawal string is relatively long, much exceeding the length of the tampon body, typically 3–5 times the length of the tampon body.

In production, the digital tampons are typically produced on high speed production lines where they are typically wrapped into individual hygienic packages. However, the conventional methods of wrapping the digital tampons have drawbacks. For example, some wrapping methods require for the withdrawal string not to be lose from the tampon body in order for the string not to interfere with the wrapping operations of the tampon. Examples of the methods for addressing the lose string problem include methods for combining the string with the tampon into a single body, such as, winding the string around the tampon or gathering and packing it internally into a cavity inside the tampon, typically, in the trailing end of the tampon (as disclosed, for example, in U.S. Pat. No. 3,863,636 issued to Johnson and U.S. Pat. No. 3,818,912 issued to Etz), and then securing the gathered string by gluing or heat sealing. However, the above steps of combining and securing the withdrawal string can be expensive and even detrimental to the tampon properties. For example, the application of heat for securing the string to the body of the tampon, especially to the self-sustained, shaped tampon (for example, the tampons disclosed in U.S. patent application Ser. No. 10/150,055, filed May 16, 2002 under Kollwitz, et al., which can be produced by the method disclosed in U.S. patent application Ser. No. 10/717,269, filed Nov. 19, 2003 under Bittner, et al., both of which are hereby incorporated by reference herein) can negatively affect the properties of the tampon.

Other wrapping methods, which do not require the combining of the string into a single body with the tampon, also have drawbacks. For example, such wrapping methods can be material dependent, i.e., requiring a wrapping material of certain rigidity, as disclosed, for example, in U.S. Pat. No. 5,471,820 issued to Oppe et al. However, such "rigid" wrapping materials can be too noisy and thus less preferable for the user in comparison with more "quiet" wrapping materials. In addition, as also disclosed in U.S. Pat. No. 5,471,820 issued to Oppe et al., such "rigid" wrapping materials can require a tear strip to facilitate the opening of the package, which can also add to the cost.

Furthermore, the wrapping method disclosed in U.S. Pat. No. 5,471,820 issued to Oppe et al., requires the application of heat to seal the wrapping material around the tampon end. However, as noted above, such heat application can be detrimental to the new digital tampons, disclosed in U.S. patent application Ser. No. 10/150,055 under Kollwitz, et al.

In addition, the conventional wrapping methods can be shape-dependent, i.e., preferring relatively straight, cylindrical tampons. However, the new digital tampons, such as the self-sustained, shaped tampons disclosed in the above noted U.S. patent application Ser. No. 10/150,055 to Kollwitz, et al., can have shapes that differ from the relatively straight, cylindrical tampons.

Therefore, it would be beneficial to provide a method of wrapping digital tampons that is capable of utilizing a broad range of wrapping materials, including, for example, "quiet" materials and/or materials that do not require the use of a tear strip for opening the package. Further, it would be beneficial to provide a method of wrapping digital tampons that does not require application of heat and/or glue for securing a withdrawal string to the body of the tampon. Furthermore, it would be beneficial to provide a method of wrapping digital tampons that is capable of wrapping various shape tampons.

SUMMARY OF THE INVENTION

In response to the above drawbacks of the prior art, a new method of wrapping digital tampons has been discovered. The method comprises the following steps:

(a) providing a continuous web of a wrapping material extending generally horizontally in a machine direction;

(b) folding the wrapping material into a trough having an open top;

(c) providing a single-file flow of digital tampons having a longitudinal centerline oriented in the machine direction, the tampons being separated from each other, each tampon having one end of the withdrawal string attached thereto and another end of the withdrawal string being held by a transporting device such that the withdrawal string extends from the tampon into the transporting device;

(d) feeding the tampon in the machine direction into the trough by the transporting device extending through the open top of the trough;

(e) sealing the trough to form a preliminary end seal disposed adjacent to an end of the digital tampon to provide a dividing wall between the adjacent tampons;

(f) releasing the withdrawal string from the transporting device;

(g) removing the transporting device from the trough;

(h) sealing the trough to provide a longitudinal seal forming a tube from the trough;

(i) sealing the tube to provide a first end seal and a second end seal; and (j) severing the tube along the first end seal and the second end seal to form a wrapped package containing the digital tampon with the withdrawal string attached thereto.

In other aspect of the invention, the method can comprise the step of folding the tube longitudinally prior to making a first and a second end seals to reduce the width of the wrapped package.

BRIEF DESCRIPTION OF THE DRAWINGS

In the drawings, like reference numbers indicate identical or functionally similar elements.

DETAILED DESCRIPTION OF THE INVENTION

Figure 1:
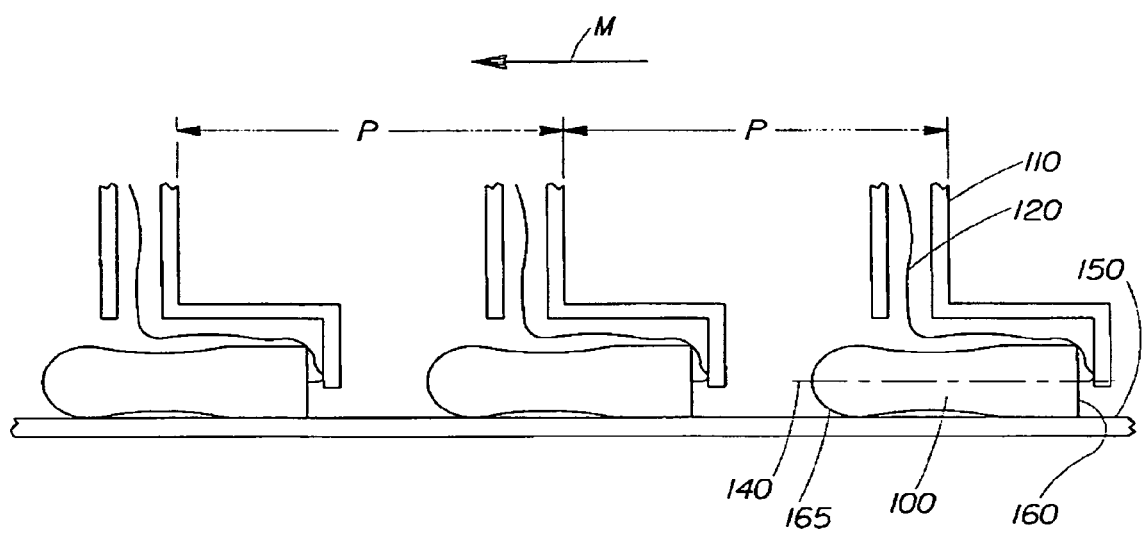
FIG. 1 is a schematic illustration of a single-file flow of digital tampons and transporting devices pushing digital tampons in a machine direction and holding withdrawal strings, attached to the tampons, such that the withdrawal strings do not interfere with wrapping operations.

Referring to FIG. 1, which is a schematic illustration of a single-file flow of digital tampons 100 and transporting devices 110 pushing digital tampons 100 in a machine direction M and holding withdrawal strings 120, attached to the tampons 100, such that the withdrawal strings 120 do not interfere with subsequent wrapping operations described below.

The tampon 100 can be any digital tampon, of any shape and size, including relatively straight, cylindrical tampons or any other shape tampons, including the digital tampons disclosed in U.S. patent application Ser. No. 10/150,055, filed May 16, 2002 under Kollwitz, et al., which can be produced by the method disclosed in U.S. patent application Ser. No. 10/717,269, filed Nov. 19, 2003 under Bittner, et al., both of which are hereby incorporated by reference herein.

One end of the withdrawal string 120 is attached to the tampon 100 by any suitable means and at any suitable place of the tampon 100. However, in the exemplary embodiment of the tampon 100 shown in the figures, the withdrawal string 120 is attached to the trailing end 160 of the tampon 100.

The tampons 100 are preferably oriented in the machine direction M along their longitudinal centerline 140 such that a trailing end 160 of the tampon 100 is trailing a tip end 165 of the tampon 100. However, it should be noted that conversely the tampons 100 can be oriented in the machine direction M such that the tip end 165 of the tampon 100 trails the trailing end 160. The tampons 100 can be supported by any suitable surface 150.

Figure 13:
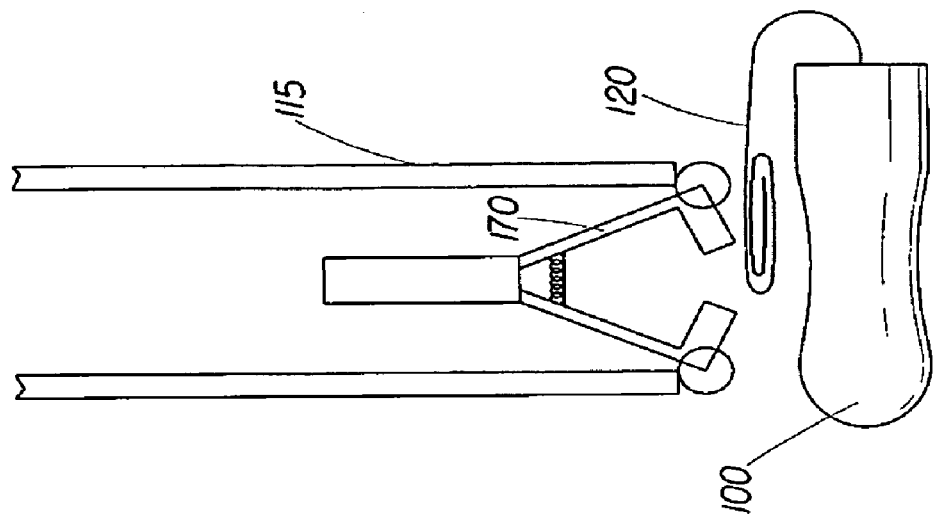
FIG. 13 is an illustration of the transporting device of FIG. 12, releasing the withdrawal string.
Figure 12:
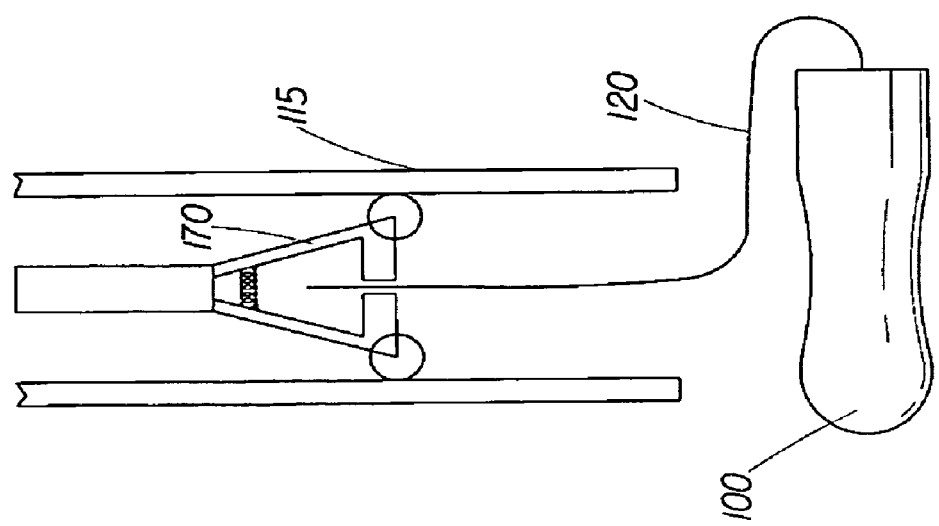
FIG. 12 is an alternative embodiment of a transporting device comprising a mechanical means for gripping and releasing the withdrawal string.

The transporting device 110 comprises preferably a vacuum means for sucking the withdrawal string 120 so the withdrawal string 120 extends from the tampon 100 into the transporting device 110. However, alternatively to the vacuum means, the transporting device 100 can comprise a suitable mechanical means for extending the withdrawal string 110 from the tampon 100. For example, FIGS. 12 and 13 illustrate one embodiment of a transporting device 115 having a mechanical means in a form of a gripper 170 capable to hold and pull the withdrawal string 110 (as shown in FIG. 12) and to release the withdrawal string 110 at a desired time (as shown in FIG. 13).

The transporting devices 110 can be attached to any suitable conveying means, for example, an overhead conveyor comprising an endless belt or a chain to provide a single-file flow of transporting devices 110 traveling in the machine direction M at a suitable velocity and being separated from each other at a pitch distance P (shown in FIG. 1).

Figure 2:
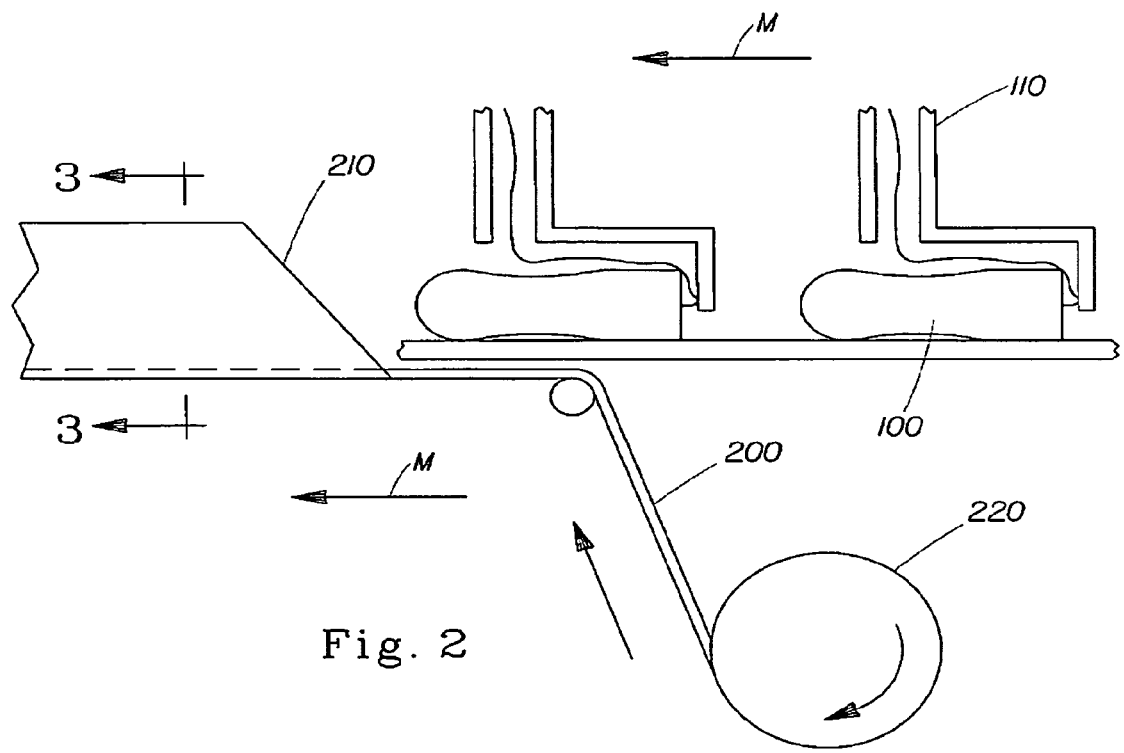
FIG. 2 is a schematic illustration of the single-file flow of digital tampons and transporting devices of FIG. 1 and a wrapping material folded into a trough for accepting the tampons.
Figure 3:
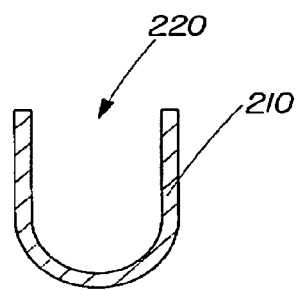
FIG. 3 is a cross-sectional view of the trough taken along section line 3—3 of FIG. 2.

Referring to FIG. 2, which is a schematic illustration of the single-file flow of digital tampons 100 and transporting devices 110 of FIG. 1 before entering a trough 210 formed by folding a wrapping material 200. The wrapping material 200 can be any material suitable for use for hygienic packaging of tampons. The wrapping material 200 can be provided from a suitable storage roll 220 by any suitable means known in production of disposable hygienic articles. The wrapping material 200 can be folded into the trough 210 having an open top 220 (as shown, for example, in FIG. 3) by any suitable means (not shown) known in the art of folding continuous web materials. The trough 210 can be pulled in the machine direction M at any suitable speed by any suitable means known in the art, including any suitable metering device (not shown) disposed downstream of the operations disclosed below.

In a preferred embodiment of the present invention, the open top 220 of the trough 210 and the transporting devices 110 are disposed substantially vertically; however, other suitable orientations, including, for example, a substantially horizontal or an inclined orientations have been also contemplated by the applicants.

Figure 4:
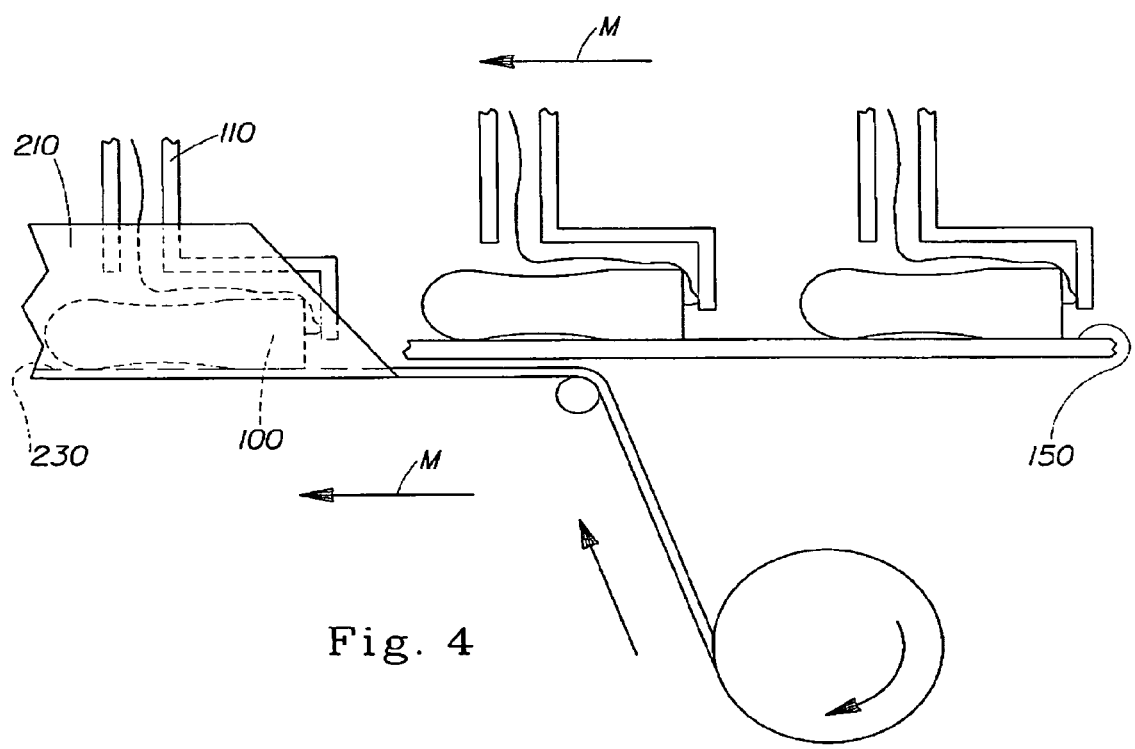
FIG. 4 is a schematic illustration of the digital tampon being pushed into the trough of FIG. 2.

After the folding of the trough 210, the tampon 100 is pushed by the transporting device 110 from the supporting surface 150 into the trough 210, as illustrated in FIG. 4. Now the tampon 100 is supported by the inner surface 230 of the trough 210.

Figure 5:
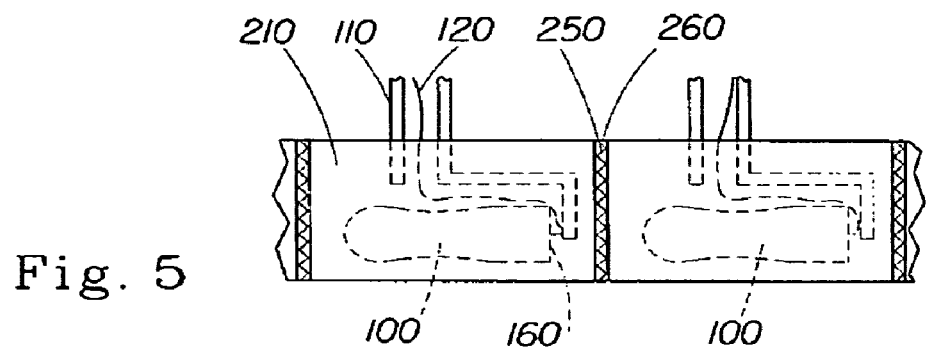
FIG. 5 is a schematic illustration of the digital tampon in the trough of FIG. 4 after sealing the trough to provide a dividing barrier between adjacent tampons, wherein, for clarity, the tampon and transporting device are shown visible.
Figure 6:
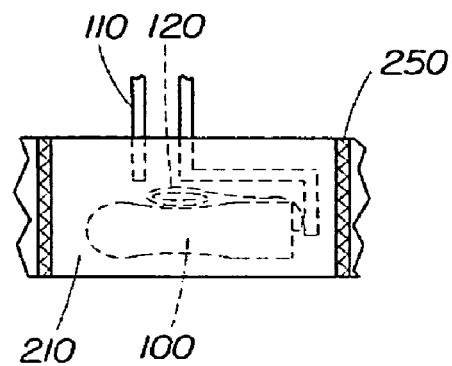
FIG. 6 is a schematic illustration of the digital tampon in the trough of FIG. 5 after releasing the withdrawal string from the transporting device, wherein, for clarity of illustration, the tampon and the transporting device are shown visible.

As shown in FIG. 5, in the trough 210, the tampons 100 become separated from each other by a dividing barrier 250 in a form of a preliminary end seal 260 disposed preferably adjacent to the trailing end 160 of the tampon 100. The preliminary end seal 260 can be any seal (continuous or discontinuous) suitable to provide the barrier 250 capable of containing the string 120 inside the dividing barrier 250 after the string 120 is released by the transporting device 110 into the trough 210 (as shown, for example, in FIG. 6).

During the release, for transporting devices comprising a vacuum means, the vacuum action, sucking the string 120, can be switched to a compressed air action forcing the string 120 into the trough 210. Alternatively, for transporting devices comprising a mechanical means for gripping the string 120 (as shown, for example, in FIG. 12), the mechanical action of releasing the string 120 (as shown, for example, in FIG. 13) can be assisted also by a compressed air action or a pushing rod action forcing the string 120 into the trough 210.

Figure 7:
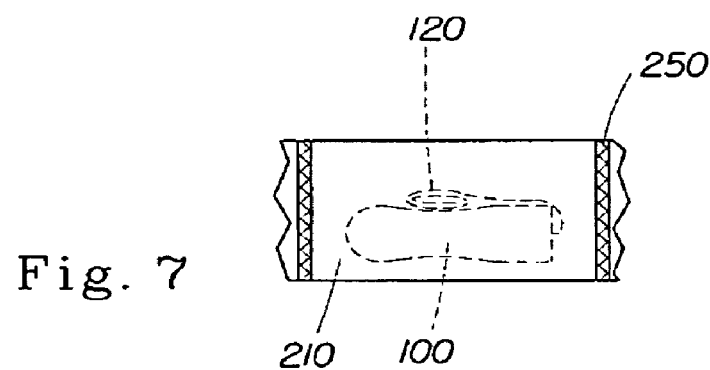
FIG. 7 is a schematic illustration of the digital tampon in the trough of FIG. 6 after removing the transporting device from the trough, wherein, for clarity of illustration, the tampon is shown visible.

After releasing the string 120, the transporting device 110 is removed from the trough 210 to enable subsequent wrapping operations. FIG. 7 is a schematic illustration of the digital tampon 100 in the trough 210 of FIG. 6 after removing the transporting device 110 from the trough 210. The transporting device 110 can be removed from the trough 210 by any suitable means including, for example, a cam, a motor, a solenoid, and the like.

Figure 8:
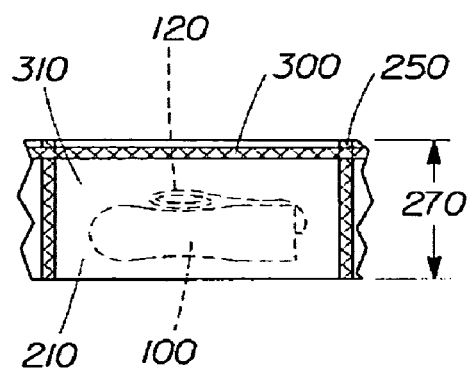
FIG. 8 is a schematic illustration of the digital tampon in the trough of FIG. 7 after sealing the trough to provide a longitudinal seal forming a tube from the trough, wherein, for clarity of illustration, the tampon is shown visible.
Figure 9:
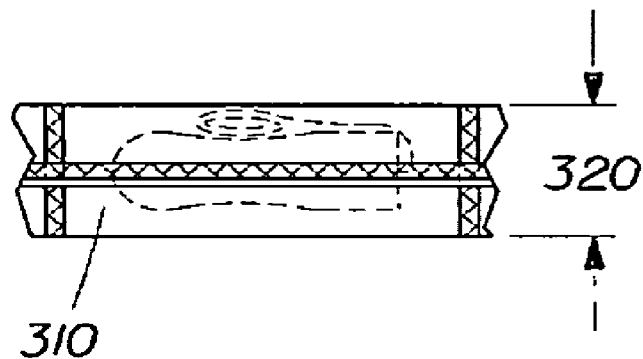
FIG. 9 is a schematic illustration of the digital tampon in the tube of FIG. 8 after folding the tube in the longitudinal direction, wherein, for clarity of illustration, the tampon is shown visible.
Figure 10:
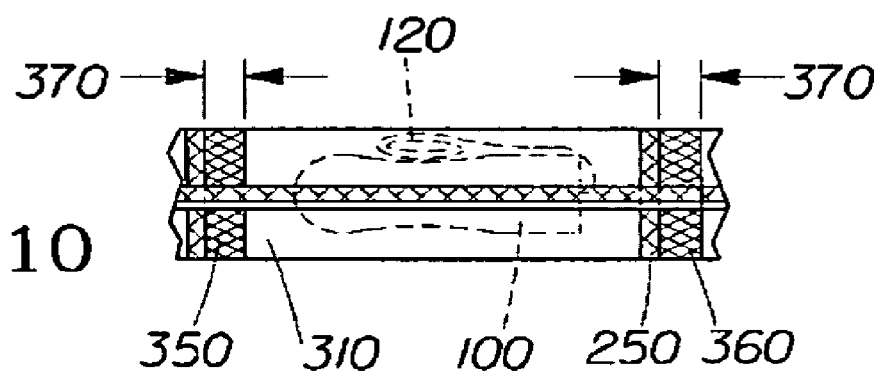
FIG. 10 is a schematic illustration of the digital tampon in the tube of FIG. 9 after sealing the tube to provide a first end seal and a second end seal, wherein, for clarity of illustration, the tampon is shown visible.

Examples of subsequent wrapping operations are shown in FIGS. 8–10. The operations include sealing the trough 210 in the machine direction M to provide a longitudinal seal 300 closing the open top 220 (FIG. 3) of the trough 210 to form a tube 310 (having a width 270) from the open top trough 210. The longitudinal seal 300 can be any suitable seal capable of providing a substantially hermetical seal.

Further operations illustrated in FIGS. 9–10 can be switched in their order of performance. As illustrated in FIG. 9, the tube 310 can be folded horizontally to reduce the width 270 (FIG. 8) of the tube 310 to a width 320. Then, as illustrated in FIG. 10, the tube 310 can be sealed to provide a first end seal 350 and a second end seal 360 to fully enclose the tampon 110 and the withdrawal string 120 inside the tube 310. The second end seal 360 is formed preferably behind the preliminary end seal 250, as shown in FIG. 10. Both the first and the second end seals 350 and 360, respectively, can be any seal suitable substantially hermetic seal having a width 370. The width 370 can be of any suitable width, both the same or different for the first and the second end seals 350 and 360, respectively.

Alternatively, the folding step of FIG. 9 can be omitted, wherein the first and the second end seals 350 and 360 of FIG. 10 are performed directly after the longitudinal seal 300 of FIG. 8 is provided.

Figure 11:
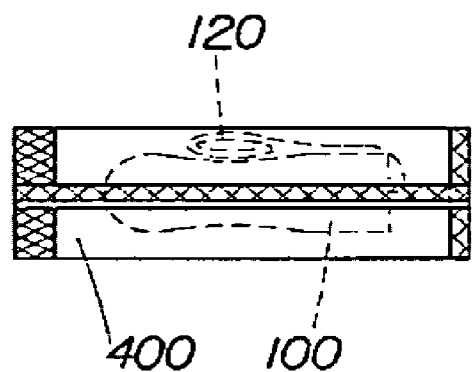
FIG. 11 is a schematic illustration of one embodiment of a wrapped package of the present invention, containing a digital tampon and a withdrawal string, after severing the tube of FIG. 10 along the first and second end seals, wherein, for clarity of illustration, the tampon is shown visible.

Finally, the tube 310 can be severed along the first and the second end seals 350 and 360, respectively, preferably severing the width 370 substantially in half to form a wrapped package 400 containing the tampon 100 and the withdrawal string 120, as shown in FIG. 11. The severing operation can be any suitable operation known in the art.

It should be noted that the method of the present invention can be applicable for wrapping not only digital tampons (i.e., tampons without applicators), but also tampons with applicators intended for inserting the tampon into a body cavity, having a withdrawal string extending from the applicator.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of individually wrapping digital tampons having a withdrawal string attached thereto, comprising the steps of:
    (a) providing a continuous web of a wrapping material extending generally horizontally in a machine direction;
    (b) folding the wrapping material into a trough having an open top;
    (c) providing a single-file flow of digital tampons having a longitudinal centerline oriented in the machine direction, the tampons being separated from each other, each tampon having one end of the withdrawal string attached thereto and another end of the withdrawal string being held by a transporting device such that the withdrawal string extends from the tampon into the transporting device;
    (d) feeding the tampon in the machine direction into the trough by the transporting device extending through the open top of the trough;
    (e) sealing the trough to form a preliminary end seal disposed adjacent to an end of the digital tampon to provide a dividing wall between the adjacent tampons;
    (f) releasing the withdrawal string from the transporting device;
    (g) removing the transporting device from the trough;
    (h) sealing the trough to provide a longitudinal seal forming a tube from the trough;
    (i) sealing the tube to provide a first end seal and a second end seal; and
    (j) severing the tube along the first end seal and the second end seal to form a wrapped package containing the digital tampon with the withdrawal string attached thereto.

2. The method of claim 1, wherein the transporting device comprises a vacuum means for extending the withdrawal string.

3. The method of claim 1, wherein the transporting device comprises a mechanical means for extending the withdrawal string.

4. The method of claim 1, wherein the transporting device is oriented substantially vertically.

5. The method of claim 1, wherein the open top of the trough is disposed substantially vertically.

6. The method of claim 1, further comprising the step of folding the tube longitudinally prior to making a first end seal and a second end seal to reduce the width of the wrapped package.

* * * * *